(12) United States Patent
Shepherd

(10) Patent No.: US 11,771,577 B2
(45) Date of Patent: Oct. 3, 2023

(54) MODULAR KNEE BRACE ASSEMBLY

(71) Applicant: ORTHO INNOVATIONS, LLC, Selbyville, DE (US)

(72) Inventor: Bryan Shepherd, Selbyville, DE (US)

(73) Assignee: Ortho Innovations, LLC, Selbyville, DE (US)

( * ) Notice: Subject to any disclaimer, the term of this patent is extended or adjusted under 35 U.S.C. 154(b) by 621 days.

(21) Appl. No.: 16/533,127

(22) Filed: Aug. 6, 2019

(65) Prior Publication Data

US 2021/0038415 A1 Feb. 11, 2021

(51) Int. Cl.
*A61F 5/01* (2006.01)
*A61F 5/058* (2006.01)
*A47C 20/00* (2006.01)

(52) U.S. Cl.
CPC .......... *A61F 5/0106* (2013.01); *A47C 20/021* (2013.01); *A61F 5/0585* (2013.01); *A61F 2005/0167* (2013.01)

(58) Field of Classification Search
CPC .... A61F 5/0106; A61F 5/0585; A61F 5/0111; A61F 5/013; A61F 5/0127; A61F 5/0113; A61F 2005/0167; A61F 13/061; A61F 13/062; A61F 13/065; A61F 13/066; A47C 20/021; A43B 7/141; A43B 7/142; A43B 7/143; A43B 17/14; A43B 17/16
USPC .............. 602/16, 26, 27, 65; 128/882; 36/44
See application file for complete search history.

(56) References Cited

U.S. PATENT DOCUMENTS

| | | | |
|---|---|---|---|
| 4,041,940 A | 8/1977 | Frankel | |
| 4,889,109 A | 12/1989 | Gifford | |
| 4,910,818 A * | 3/1990 | Grabill | A47C 20/021 5/494 |
| 5,125,123 A * | 6/1992 | Engle | A47C 20/025 128/845 |
| 5,216,771 A * | 6/1993 | Hoff | A47C 20/025 5/652 |
| 5,418,991 A | 5/1995 | Shiflett | |
| 6,640,368 B2 | 11/2003 | Roston | |
| 6,935,697 B2 | 8/2005 | Conlon | |
| D646,790 S | 10/2011 | Castillo | |
| 2007/0185423 A1* | 8/2007 | Brown | A61F 5/0106 602/5 |
| 2017/0197818 A1* | 7/2017 | Berreklouw | B68C 1/147 |

* cited by examiner

*Primary Examiner* — Alireza Nia
*Assistant Examiner* — Michael Milo
(74) *Attorney, Agent, or Firm* — Dickinson Wright PLLC

(57) ABSTRACT

A modular knee brace assembly includes a brace that is worn around a knee after orthopedic surgery has been performed on the knee. A wedge is removably coupled to the brace when the brace is worn around the knee. The wedge is positioned on a back side of the knee to support the knee in a bent position when the user is lying on the user's back. An inner knee support is removably coupled to the brace when the brace is worn around the knee. The inner knee support extends between each of the user's knees when the user lies on their side. An outer knee support is removably coupled to the brace when the brace is worn around the knee. In this way the outer knee support supports the knee when the user lies on the user's side.

11 Claims, 5 Drawing Sheets

MODULAR KNEE BRACE ASSEMBLY

CROSS-REFERENCE TO RELATED APPLICATIONS

Statement Regarding Federally Sponsored Research or Development

Not Applicable

The Names of the Parties to a Joint Research Agreement

Not Applicable

Incorporation-by-Reference of Material Submitted on a Compact Disc or as a Text File Via the Office Electronic Filing System Not Applicable Statement Regarding Prior Disclosures by the Inventor or Joint Inventor Not Applicable

BACKGROUND OF THE INVENTION (1) Field of the Invention (2) Description of Related Art Including Information Disclosed Under 37 CFR 1.97 and 1.98

The disclosure and prior art relates to knee brace devices and more particularly pertains to a new knee brace device for supporting a knee in a plurality of sleeping positions.

BRIEF SUMMARY OF THE INVENTION

An embodiment of the disclosure meets the needs presented above by generally comprising a brace that is worn around a knee after orthopedic surgery has been performed on the knee. A wedge is removably coupled to the brace when the brace is worn around the knee. The wedge is positioned on a back side of the knee to support the knee in a bent position when the user is lying on the user's back. An inner knee support is removably coupled to the brace when the brace is worn around the knee. The inner knee support extends between each of the user's knees when the user lies on their side. An outer knee support is removably coupled to the brace when the brace is worn around the knee. In this way the outer knee support supports the knee when the user lies on the user's side.

There has thus been outlined, rather broadly, the more important features of the disclosure in order that the detailed description thereof that follows may be better understood, and in order that the present contribution to the art may be better appreciated.

There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
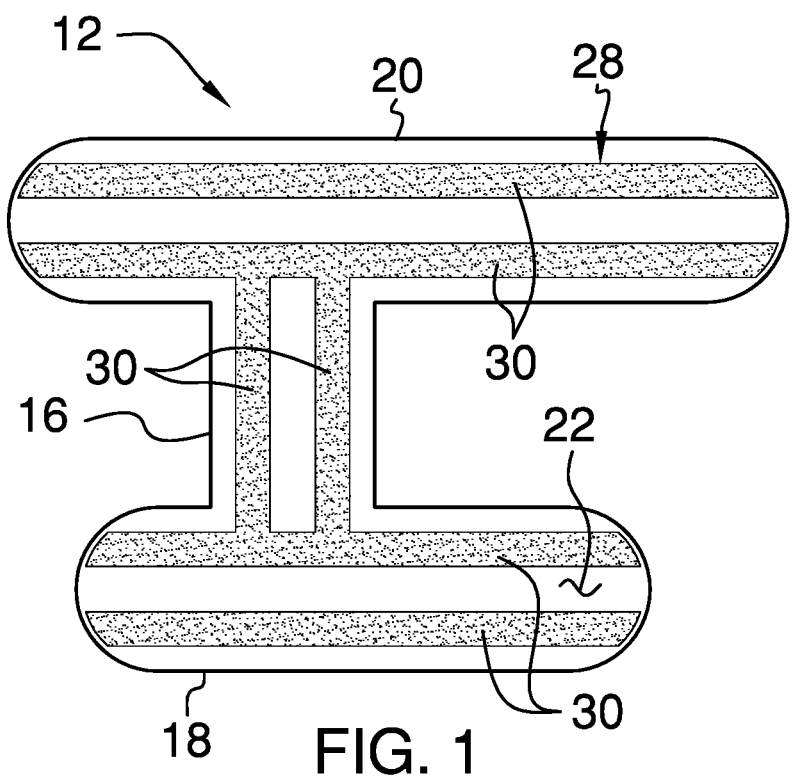
FIG. 1 is a top view of a brace of a modular knee brace assembly according to an embodiment of the disclosure.
Figure 2:
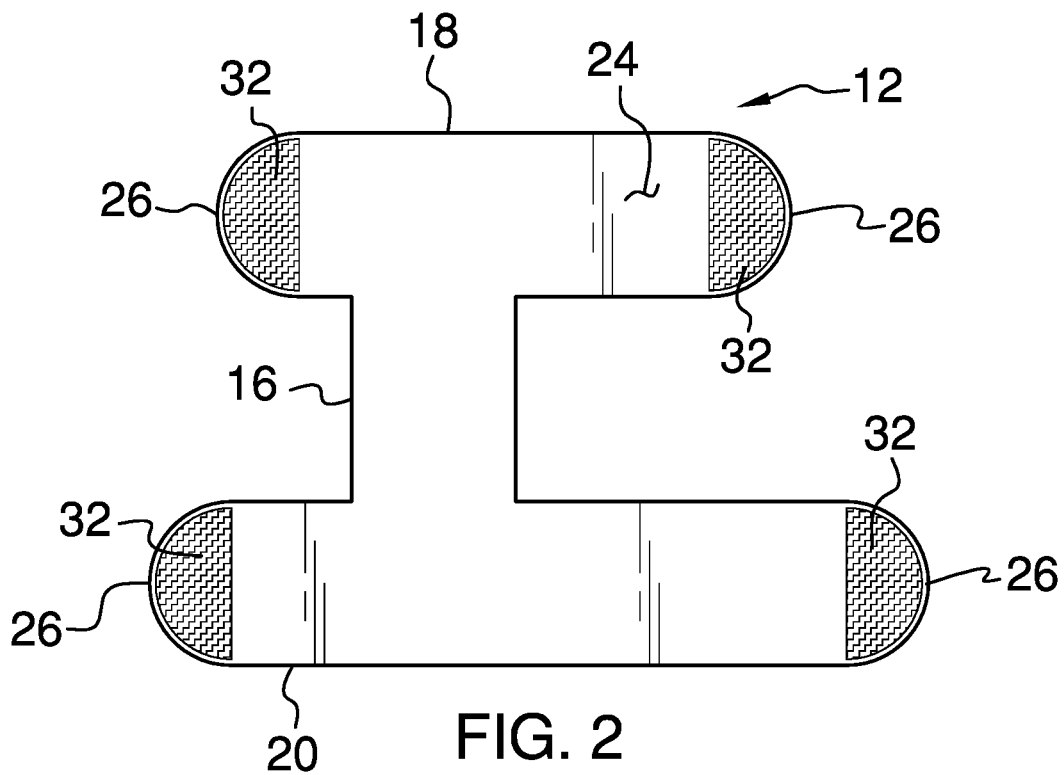
FIG. 2 is a bottom view of a brace of an embodiment of the disclosure.
Figure 3:
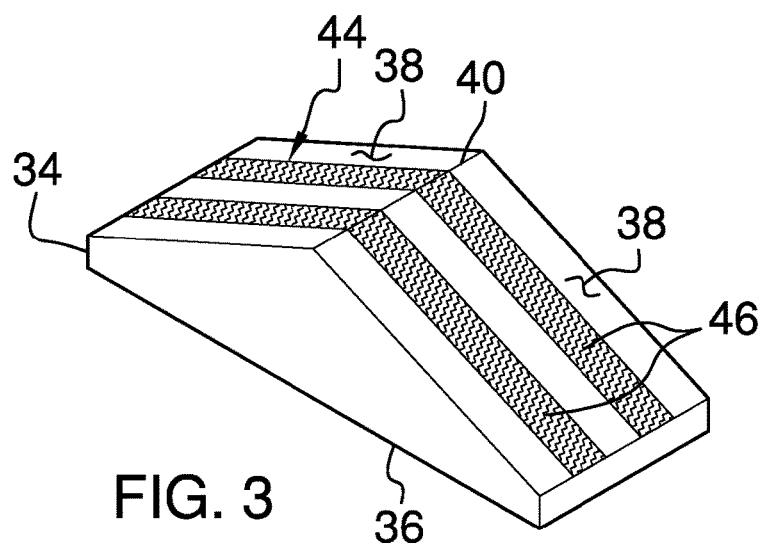
FIG. 3 is a top perspective view of a wedge of an embodiment of the disclosure.
Figure 4:
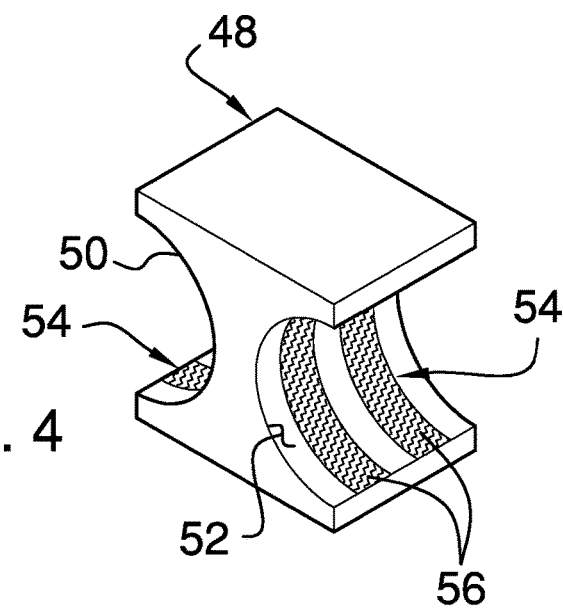
FIG. 4 is a front perspective view of an inner knee support of an embodiment of the disclosure.
Figure 5:
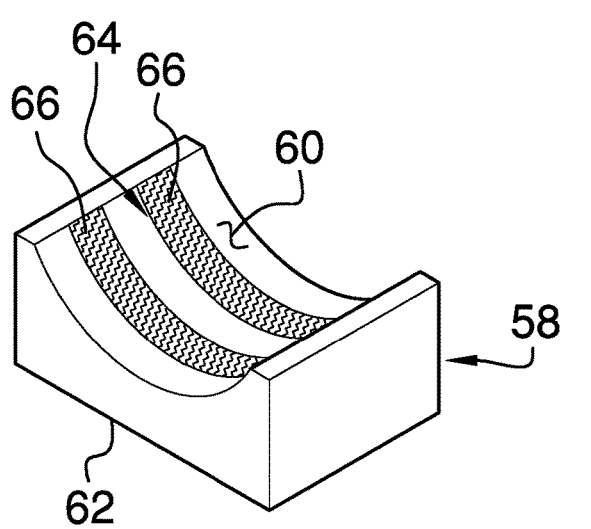
FIG. 5 is a perspective view of an outer knee support of an embodiment of the disclosure.

With reference now to the drawings, and in particular to FIGS. 1 through 8 thereof, a new knee brace device embodying the principles and concepts of an embodiment of the disclosure and generally designated by the reference numeral 10 will be described.

As best illustrated in FIGS. 1 through 8, the modular knee brace assembly 10 generally comprises a brace 12 that is worn around a knee 14 after orthopedic surgery has been performed on the knee 14. The brace 12 comprises a first panel 16 extending between a second panel 18 and a third panel 20. The first panel 16 is oriented at a right angle with each of the second 18 and third 20 panels such that the brace 12 has an I shape. Additionally, the first panel 16 extends along an axis that is offset from a lateral centerline of each of the second 18 and third 20 panels. The second panel 18 has a length that is shorter than a length of the third panel 20.

Each of the first 16, second 18 and third 20 panels has a top surface 22 and a bottom surface 24, and each of the second 18 and third 20 panels has a pair of distal ends 26 with respect to the first panel 16. The bottom surface 24 is wrapped around the knee 14 having the top surface 22 being exposed. The second panel 18 is wrapped around the user's upper calf, the third panel 20 is wrapped around the user's lower thigh and the first panel 16 extends vertically along a back of the user's knee 14.

A first mating unit 28 is coupled to the brace 12 and the first mating unit 28 is exposed when the brace 12 is worn around the knee 14. The first mating unit 28 comprises a plurality of sets of strips 30. Each of the sets of strips 30 is positioned on the top surface 22 of a respective one of the first 16, second 18 and third 20 panels. Moreover, each of the sets of strips 30 is coextensive with the respective first 16, second 18 and third 20 panels. The set of strips 30 on the first panel 16 intersects the set of strips 30 on each of the second 18 and third 20 panels.

A plurality of mating members 32 is each coupled to the brace 12. Each of the mating members 32 releasably engages the first mating unit 28 when the brace 12 is wrapped around the knee 14 for retaining the brace 12 around the knee 14.

Each of the mating members 32 is positioned on the bottom surface 24 of a respective one of the second 18 and third 20 panels. Additionally, each of the mating members 32 is aligned with a respective one of the distal ends 26 of the respective second 18 and third 20 panels. Each of the mating members 32 releasably engages the set of strips 30 on the respective second 18 and third 20 panels. Each of the mating members 32 and each of the strips 30 may comprise hook and loop fasteners or the like.

A wedge 34 is removably coupled to the brace 12 when the brace 12 is worn around the knee 14. The wedge 34 is positioned on a back side of the knee 14 to support the knee 14 in a bent position when the user is lying on the user's back. The wedge 34 has a basal surface 36 extending between a pair of top surfaces 38, and the top surfaces 38 are oriented at an angle with each other. Each of the top surfaces 38 abuts the top surface 22 of a respective one of the second 18 and third 20 panels when the brace 12 is worn on the knee 14. A peak 40 of the top surfaces 38 is aligned with a back of the knee 14 thereby supporting the knee 14 in a bent position. The basal surface 36 abuts a support surface 42 upon which the user is lying thereby supporting the knee 14 in the bent position. The wedge 34 may be comprised of a resiliently compressible material for enhancing comfort for the user.

A second mating unit 44 is coupled to the wedge 34 and the second mating unit 44 releasably engages the first mating unit 28 to retain the wedge 34 on the brace 12. The second mating unit 44 comprises a set of strips 46 that is positioned on each of the top surfaces 38 of the wedge 34. The set of strips 46 of the second mating unit 44 is coextensive with each of the top surfaces 38 of the wedge 34. Moreover, each of the strips 46 of the second mating unit 44 releasably engages respective ones of the strips 30 of the first mating unit 28. Each of the strips 46 of the second mating unit 44 may comprise hook and loop fasteners or the like.

An inner knee support 48 is removably coupled to the brace 12 when the brace 12 is worn around the knee 14. The inner knee support 48 extends between each of the user's knees 14 when the user lies on their side. Moreover, the inner knee support 48 is positioned on an interior side of the knee 14 to support the knee 14 when the user lies on their side opposite of the knee 14 on which the brace 12 is worn. The inner knee support 48 has a first lateral surface 50 and a second lateral surface 52. Each of the first 50 and second 52 lateral surfaces is concavely arcuate with respect to each other to conform to the curvature of a respective one of the user's knees 14 when the user lies on the user's side. The inner knee support 48 is positioned on the user's thigh above the knee 14. The inner knee support 48 may be comprised of a resiliently compressible material for enhancing comfort for the user.

A pair of third mating units 54 is each coupled to the inner knee support 48. Respective ones of the third mating units 54 releasably engage the first mating unit 28 to retain the inner knee support 48 on the brace 12. Each of the third mating units 54 comprises a set of strips 56 and each of the strips 56 of each of the third mating units 54 is positioned on a respective one of the first 50 and second 52 lateral surfaces of the inner knee support 48. Each of the strips 56 on a respective one of the first 50 or second 52 lateral surfaces releasably engages respective ones of the strips 30 of the first mating unit 28. Additionally, each of the strips 56 of the third mating units 54 may comprise a hook and loop fastener or the like.

An outer knee support 58 is removably coupled to the brace 12 when the brace 12 is worn around the knee 14 to support the knee 14 when the user lies on the user's side. The outer knee support 58 is positioned on an outer side of the knee 14 to support the knee 14 when the user lies on the outer side of the knee 14. The outer knee support 58 has a first surface 60 that is concavely arcuate with respect to a second surface 62 such that the first surface 60 can conform to the curvature of the knee 14. The second surface 62 abuts the support surface 42 when the user lies on the user's side. The outer knee support 58 may be comprised of a resiliently compressible material to enhance comfort for the user.

A fourth mating unit 64 is coupled to the outer knee support 58. The fourth mating unit 64 releasably engages the first mating unit 28 to retain the outer knee support 58 on the brace 12. The fourth mating unit 64 comprising a set of strips 66 and each of the strips 66 of the fourth mating unit 64 is positioned on the first surface 60 of the outer knee support 58. Each of the strips 66 of the fourth mating unit 64 releasably engages respective ones of the strips 30 of the first mating unit 28. Additionally, each of the strips 66 of the fourth mating unit 64 may comprise a hook and loop fastener or the like.

Figure 6:
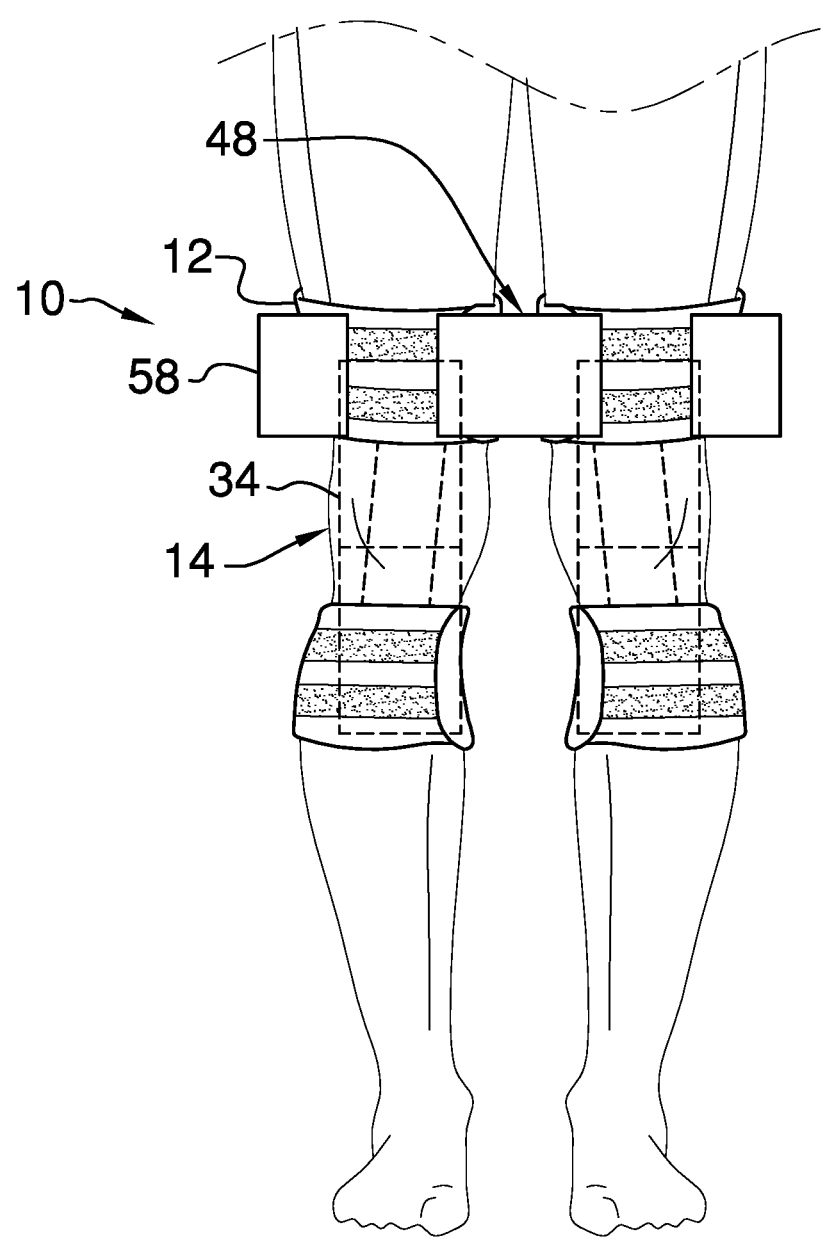
FIG. 6 is a front in-use view of an embodiment of the disclosure.
Figure 7:
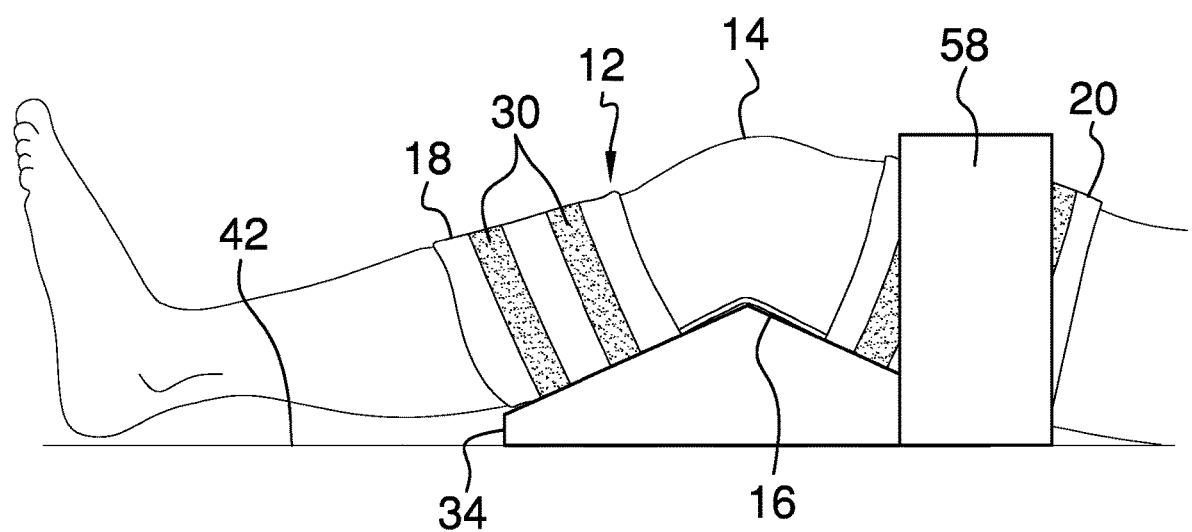
FIG. 7 is a perspective in-use view of an embodiment of the disclosure.
Figure 8:
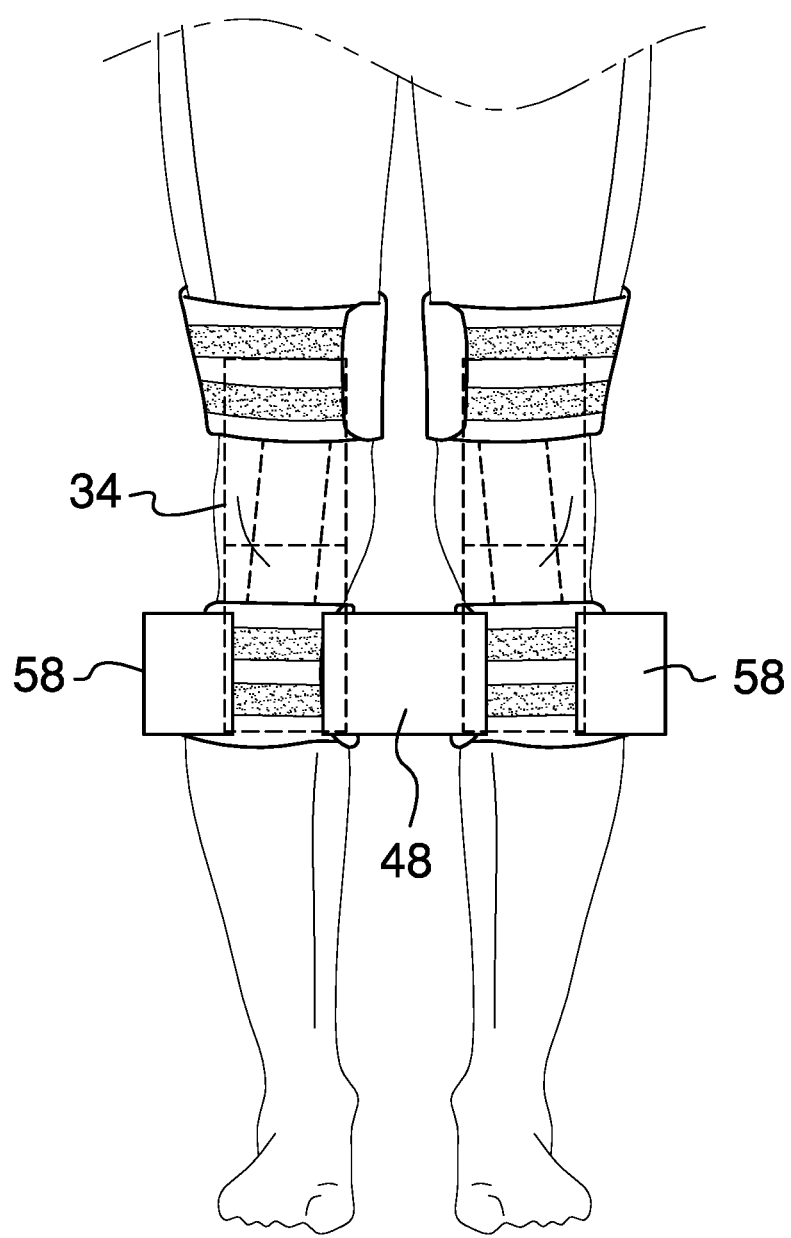
FIG. 8 is a front perspective in-use view of an embodiment of the disclosure.

As is most clearly shown in FIG. 6, a pair of the braces 12 may each be worn around a respective one of the user's knees 14. The inner knee support 48 can be coupled between each of the braces 12. Additionally, a pair of the outer knee supports 58 may each be coupled to a respective one of the braces 12. In this way each of the knees 14 are supported regardless of which side the user is lying on. A pair of the wedges 34 may each be coupled to a respective one of the braces 12 to support each of the knees 14 when the user is lying on their back. As is most clearly shown in FIG. 8, the inner knee support 48 and the outer knee support 58 can be aligned with each of the user's knees.

In use, the brace 12 is worn around the user's knee 14. The wedge 34 is coupled to the brace 12 and the wedge 34 is positioned on the back side of the knee 14. The inner knee support 48 is coupled to the brace 12 and the inner knee support 48 is positioned on the interior side of the knee 14. The outer knee support 58 is coupled to the brace 12 and the outer knee support 58 is positioned on the outer side of the knee 14 support. In this way the user's knee 14 is supported regardless if the user is sleeping on their back, their right side or their left side. Moreover, the brace 12, the wedge 34, the inner knee support 48 and the outer knee support 58 reduce pain during sleeping and enhance the healing process.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A modular knee brace assembly being configured to be worn on a knee after orthopedic surgery such that said assembly supports the knee in any lying position, said modular knee brace assembly comprising:
    a brace configured to be worn around the knee after orthopedic surgery has been performed on the knee;
    a first mating unit being coupled to said brace, said first mating unit being exposed when said brace is worn around the knee;
    a plurality of mating members, each of said mating members being coupled to said brace, each of said mating members releasably engaging said first mating unit when said brace is wrapped around the knee for retaining said brace around the knee;
    a wedge being removably coupled to said brace when said brace is worn around the knee, said wedge being configured to be positioned on a back side of the knee wherein said wedge is configured to support the knee in a bent position when a user is lying on a user's back;
    a second mating unit being coupled to said wedge, said second mating unit releasably engaging said first mating unit to retain said wedge on said brace;
    an inner knee support being removably coupled to said brace when said brace is worn around the knee wherein said inner knee support is configured to extend between each knee of the user when the user lies on their side;
    a pair of third mating units, each of said third mating units being coupled to said inner knee support, respective ones of said third mating units releasably engaging said first mating unit to retain said inner knee support on said brace;
    an outer knee support, said outer knee support being removably coupled to said brace when said brace is worn around the knee wherein said outer knee support is configured to support the knee when the user lies on the user's side; and
    a fourth mating unit being coupled to said outer knee support, said fourth mating unit releasably engaging said first mating unit to retain said outer knee support on said brace.

2. The modular knee brace assembly according to claim 1, wherein:
    said brace comprises a first panel extending between a second panel and a third panel, said first panel being oriented at a right angle with each of said second and third panels such that said brace has an I shape, said first panel extending along an axis being offset from a lateral centerline of each of said second and third panels, said second panel having a length being shorter than a length of said third panel, each of said first, second and third panels having a top surface and a bottom surface, each of said second and third panels having a pair of distal ends with respect to said first panel; and
    said bottom surface is configured to be wrapped around the knee having said top surface being exposed, said second panel configured to be wrapped around a user's upper calf, said third panel configured to be wrapped around a user's lower thigh, said first panel configured to extend vertically along a back of the user's knee.

3. The modular knee brace assembly according to claim 2, wherein said first mating unit comprises a plurality of sets of strips, each of said sets of strips being positioned on said top surface of a respective one of said first, second and third panels, each of said sets of strips being coextensive with said respective first, second and third panels, said set of strips on said first panel intersecting said set of strips on each of said second and third panels.

4. The modular knee brace assembly according to claim 3, wherein said wedge has a basal surface extending between a pair of top surfaces, said pair of top surfaces being oriented at an angle with each other, each of said top surfaces abutting said top surface of a respective one of said second and third panels when said brace is worn on the knee having a peak of said pair of top surfaces being aligned with the back side of the knee wherein said wedge is configured to support the knee in a bent position, said basal surface being configured to abut a support surface upon which the user is lying thereby supporting the knee in the bent position.

5. The modular knee brace assembly according to claim 4, wherein said second mating unit comprises a set of strips being positioned on each of said pair of top surfaces of said wedge, said set of strips of said second mating unit being coextensive with each of said top surfaces of said wedge, each of said strips of said second mating unit releasably engaging respective ones of said strips of said first mating unit.

6. The modular knee brace assembly according to claim 5, wherein each of said third mating units comprises a set of strips, each of said strips of each of said third mating units being positioned on a respective one of said first and second lateral surfaces of said inner knee support, each of said strips on a respective one of said first or second lateral surfaces releasably engaging respective ones of said strips of said first mating unit.

7. The modular knee brace assembly according to claim 3, wherein said outer knee support is configured to be positioned on an outer side of the knee wherein said outer knee support is configured to support the knee when the user lies on the outer side of the knee, said outer knee support having a first surface being concavely arcuate with respect to a second surface wherein said first surface is configured to conform to a curvature of the knee, said second surface being configured to abut the support surface when the user lies on the user's side.

8. The modular knee brace assembly according to claim 7, wherein said fourth mating unit comprises a set of strips, each of said strips of said fourth mating unit being positioned on said first surface of said outer knee support, each of said strips of said fourth mating unit releasably engaging respective ones of said strips of said first mating unit.

9. The modular knee brace assembly according to claim 3, wherein each of said mating members is positioned on said bottom surface of a respective one of said second and third panels, each of said mating members being aligned with a respective one of said distal ends of said respective second and third panels, each of said mating members releasably engaging said set of strips on said respective second and third panels.

10. The modular knee brace assembly according to claim 3, wherein said inner knee support is configured to be positioned on an interior side of the knee wherein said inner knee support is configured to support the knee when the user lies on their side opposite of the knee on which said brace is worn, said inner knee support having a first lateral surface and a second lateral surface, each of said first and second lateral surfaces being concavely arcuate with respect to each other wherein each of said first and second lateral surfaces is configured to conform to a curvature of a respective one of the user's knees when the user lies on the user's side, said inner knee support being configured to be positioned on the user's lower thigh above the knee.

11. A modular knee brace assembly being configured to be worn on a knee after orthopedic surgery such that said assembly supports the knee in any lying position, said modular knee brace assembly comprising:
- a brace being worn around the knee after orthopedic surgery has been performed on the knee, said brace comprising a first panel extending between a second panel and a third panel, said first panel being oriented at a right angle with each of said second and third panels such that said brace has an I shape, said first panel extending along an axis being offset from a lateral centerline of each of said second and third panels, said second panel having a length being shorter than a length of said third panel, each of said first, second and third panels having a top surface and a bottom surface, each of said second and third panels having a pair of distal ends with respect to said first panel, said bottom surface configured to be wrapped around the knee having said top surface being exposed, said second panel configured to be wrapped around a user's upper calf, said third panel configured to be wrapped around a user's lower thigh, said first panel configured to extend vertically along a back of a user's knee;
- a first mating unit being coupled to said brace, said first mating unit being exposed when said brace is worn around the knee, said first mating unit comprising a plurality of sets of strips, each of said sets of strips being positioned on said top surface of a respective one of said first, second and third panels, each of said sets of strips being coextensive with said respective first, second and third panels, said set of strips on said first panel intersecting said set of strips on each of said second and third panels;
- a plurality of mating members, each of said mating members being coupled to said brace, each of said mating members releasably engaging said first mating unit when said brace is wrapped around the knee for retaining said brace around the knee, each of said mating members being positioned on said bottom surface of a respective one of said second and third panels, each of said mating members being aligned with a respective one of said distal ends of said respective second and third panels, each of said mating members releasably engaging said set of strips on said respective second and third panels;
- a wedge being removably coupled to said brace when said brace is worn around the knee, said wedge being positioned on a back side of the knee wherein said wedge is configured to support the knee in a bent position when the user is lying on the user's back, said wedge having a basal surface extending between a pair of top surfaces, said top surfaces being oriented at an angle with each other, each of said pair of top surfaces abutting said top surface of a respective one of said second and third panels when said brace is worn on the knee having a peak of said pair of top surfaces being aligned with the back side of the knee wherein said wedge is configured to support the knee in a bent position, said basal surface being configured to abut a support surface upon which the user is lying thereby supporting the knee in the bent position;
- a second mating unit being coupled to said wedge, said second mating unit releasably engaging said first mating unit to retain said wedge on said brace, said second mating unit comprising a set of strips being positioned on each of said pair of top surfaces of said wedge, said set of strips of said second mating unit being coextensive with each of said top surfaces of said wedge, each of said strips of said second mating unit releasably engaging respective ones of said strips of said first mating unit;
- an inner knee support being removably coupled to said brace when said brace is configured to be worn around the knee wherein said inner knee support is configured to extend between each of the user's knees when the user lies on their side, said inner knee support being configured to be positioned on an interior side of the knee wherein said inner knee support is configured to support the knee when the user lies on their side opposite of the knee on which said brace is worn, said inner knee support having a first lateral surface and a second lateral surface, each of said first and second lateral surfaces being concavely arcuate with respect to each other wherein each of said first and second lateral surfaces is configured to conform to a curvature of a respective one of the user's knees when the user lies on the user's side, said inner knee support being configured to be positioned on the user's lower thigh above the knee;
- a pair of third mating units, each of said third mating units being coupled to said inner knee support, respective ones of said third mating units releasably engaging said first mating unit to retain said inner knee support on said brace, each of said third mating units comprising a set of strips, each of said strips of each of said third mating units being positioned on a respective one of said first and second lateral surfaces of said inner knee support, each of said strips on a respective one of said first or second lateral surfaces releasably engaging respective ones of said strips of said first mating unit;
- an outer knee support, said outer knee support being removably coupled to said brace when said brace is worn around the knee wherein said outer knee support is configured to support the knee when the user lies on the user's side, said outer knee support being positioned on an outer side of the knee wherein said outer knee support is configured to support the knee when the user lies on the outer side of the knee, said outer knee support having a first surface being concavely arcuate with respect to a second surface wherein said first surface is configured to conform to a curvature of the knee, said second surface being configured to abut the support surface when the user lies on the user's side; and
- a fourth mating unit being coupled to said outer knee support, said fourth mating unit releasably engaging said first mating unit to retain said outer knee support on said brace, said fourth mating unit comprising a set of strips, each of said strips of said fourth mating unit being positioned on said first surface of said outer knee support, each of said strips of said fourth mating unit releasably engaging respective ones of said strips of said first mating unit.

* * * * *